(12) United States Patent (10) Patent No.: US 8,183,395 B2
Falkowski et al. (45) Date of Patent: May 22, 2012

(54) COMPOSITIONS AND METHODS FOR TREATING CANCER

(75) Inventors: Paul Falkowski, Princeton, NJ (US); Eric H. Andrianasolo, Kitchener, Ontario (CA); Liti Haramaty, New Brunswick, NJ (US); Eileen White, Princeton, NJ (US); Richard Lutz, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 433 days.

(21) Appl. No.: 12/530,415

(22) PCT Filed: Mar. 5, 2008

(86) PCT No.: PCT/US2008/055977
§ 371 (c)(1),
(2), (4) Date: Sep. 8, 2009

(87) PCT Pub. No.: WO2008/109717
PCT Pub. Date: Sep. 12, 2008

(65) Prior Publication Data
US 2010/0113585 A1 May 6, 2010

Related U.S. Application Data

(60) Provisional application No. 60/904,914, filed on Mar. 5, 2007.

(51) Int. Cl.
C07D 407/06 (2006.01)
C07C 69/74 (2006.01)
C07C 69/035 (2006.01)
A61K 31/352 (2006.01)
A61K 31/215 (2006.01)
A61K 31/22 (2006.01)

(52) U.S. Cl. ........ 549/396; 560/126; 560/249; 514/456; 514/529; 514/546

(58) Field of Classification Search ............. 549/396; 560/126, 249; 514/456, 529, 546
See application file for complete search history.

(56) References Cited

U.S. PATENT DOCUMENTS
2006/0105994 A1 5/2006 Aylward et al.
2006/0148732 A1 7/2006 Gutterman et al.

OTHER PUBLICATIONS

Bishara et al., Novaxenicins A-D and xeniolides I-K, seven new diterpines from the soft coral Xenia novaebrittanniae, ScienceDirect, Tetrahedron 62 (2006) 12092-12097.

*Primary Examiner* — Bernard Dentz
(74) *Attorney, Agent, or Firm* — Fox Rothschild LLP

(57) ABSTRACT

Compounds of formulas I-IV: (I), (II), (III) (IV), wherein: $R_1$ and $R_4$-$R_{23}$ are independently selected from H and 1-3 carbon lower alkyl; and $R_2$ and $R_3$ are independently selected from H, 1-3 carbon lower O H alkyl, and —C—$R_a$, wherein $R_a$ is 1-3 carbon lower alkyl. Pharmaceutical compositions, which include any of Compounds I-IV and a pharmaceutically acceptable carrier, methods of inducing tumor cell apoptosis by administering to a patient in need thereof an effective amount of any of Compounds I-IV, and methods for obtaining any of Compounds I-IV by extracting the compound from coral are also provided.

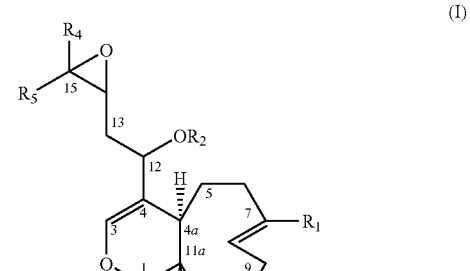

(I)

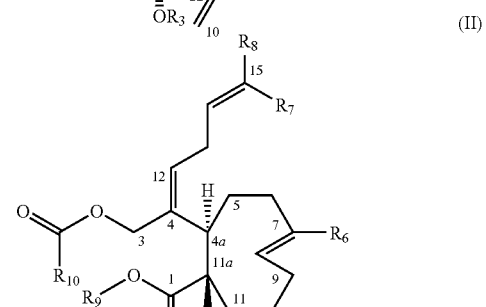

(II)

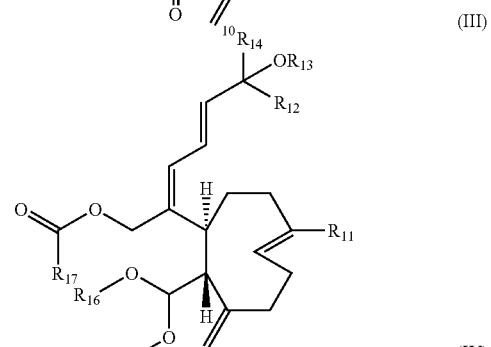

(III)

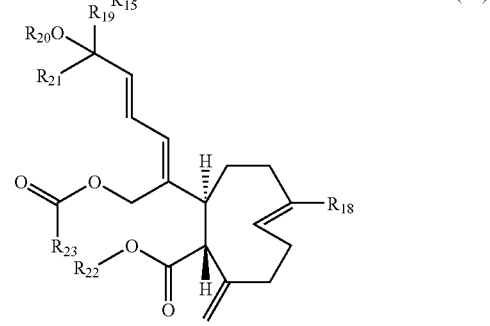

(IV)

12 Claims, 4 Drawing Sheets

| | Compound I | | |
|---|---|---|---|
| position | $\delta_C$ | $\delta_H$ | HMBC[a] |
| 1 | 91.7 CH | 5.87, d (1.3) | 3, 4a, CO |
| 3 | 140.5 CH | 6.55, s | 1, 4, 4a, 12, |
| 4 | 116.1 qC | | |
| 4a | 36.7 CH | 2.19, dd (8, 12) | 3, 4, 5, 11 |
| 5 | 30.5 $CH_2$ | 1.50, m  1.90, m | 4a, 6 |
| 6 | 40.2 $CH_2$ | 2.10, m  2.22, m | 5, 7, 8 |
| 7 | 135.7 qC | | |
| 8 | 124.3 CH | 5.40, t (5.9) | 9 |
| 9 | 25.1 $CH_2$ | 2.50, m  2.10, m | 8, 10 |
| 10 | 35.4 $CH_2$ | 2.27, m | 11, 19 |
| 11 | 151.3 qC | | |
| 11a | 49.9 CH | 1.99, dd (1.3,12) | 1, 4a, 11 |
| 12 | 72.4 CH | 5.54, t (6.2) | 3, 4, 4a, 13, 14, CO |
| 13 | 32.7 $CH_2$ | 1.96, m | 12, 14 |
| 14 | 60.9 CH | 2.73, t (5.9) | 13 |
| 15 | 58.0 qC | | |
| 16 | 19.0 $CH_3$ | 1.29, s | 14, 15, 17 |
| 17 | 24.6 $CH_3$ | 1.29, s | 14, 15, 16 |
| 18 | 17.7 $CH_3$ | 1.66, s | 6, 7, 8 |
| 19 | 113.1 $CH_2$ | 4.78, s  4.87, s | 10, 11, 11a, |
| $CH_3$ of $CH_3COO$ | 21.3 $CH_3$ | 2.06, s | CO |
| CO of $CH_3COO$ | 169.6 qC | | |
| $CH_3$ of $CH_3COO$ | 21.3 $CH_3$ | 2.04, s | CO |
| CO of $CH_3COO$ | 170.4 qC | | |

Figure 4.

|  | Compound II | | Compound III | | Compound IV | |
| --- | --- | --- | --- | --- | --- | --- |
| position | $\delta_C$ | $\delta_H$ | $\delta_C$ | $\delta_H$ | $\delta_C$ | $\delta_H$ |
| 1 | 172.7 qC | | 105.0 CH | 4.10, d (8.5) | 172.3 qC | |
| 3 | 66.5 $CH_2$ | 4.53, br s | 66.0 $CH_2$ | 4.53, br s | 66.5 $CH_2$ | 4.53, br s |
| 4 | 139.5 qC | | 140.2 qC | | 140.1 qC | |
| 4a | 39.9 CH | 3.30, m | 44.2 CH | 2.80, dd (7,12) | 44.0 CH | 2.72, m |
| 5 | 32.5 $CH_2$ | 1.45, m 1.65, m | 35.8 $CH_2$ | 2.33, m | 35.9 $CH_2$ | 2.16, m |
| 6 | 39.9 $CH_2$ | 2.10, m | 39.9 $CH_2$ | 1.86, m 2.02, m | 39.9 $CH_2$ | 1.90, m 2.01, m |
| 7 | 136.0 qC | | 135.0 qC | | 135.5 qC | |
| 8 | 124.6 CH | 5.42, m | 124.0 CH | 5.43, m | 124.5 CH | 5.43, m |
| 9 | 28.9 $CH_2$ | 2.10, m 2.40, m | 28.7 $CH_2$ | 2.09, m 2.11, m | 28.9 $CH_2$ | 2.10, m 2.38, m |
| 10 | 32.6 $CH_2$ | 2.22, m 2.43, m | 30.8 $CH_2$ | 2.16, m 2.20, m | 32.6 $CH_2$ | 2.16, m 2.23, m |
| 11 | 144.2 qC | | 144.0 qC | | 144.5 qC | |
| 11a | 61.7 CH | 3.12, d (11.0) | 56.1 CH | 1.98, d (12) | 61.8 CH | 3.13, d (12.0) |
| 12 | 130.0 CH | 5.43, m | 127.0 CH | 6.00, d (11.0) | 128.0 CH | 6.02, d (11.0) |
| 13 | 28.0 $CH_2$ | 2.80, m 2.85, m | 120.0 CH | 6.43, dd (11,15) | 121.0 CH | 6.40, dd (11,15) |
| 14 | 121.0 CH | 5.11, m | 144.2 CH | 5.93, d (15.0) | 144.0 CH | 5.70, d (15.0) |
| 15 | 133.5 qC | | 70.8 qC | | 71.5 qC | |
| 16 | 18.0 $CH_3$ | 1.64, d (1.1) | 29.4 $CH_3$ | 1.35, s | 29.5 $CH_3$ | 1.34, s |
| 17 | 25.5 $CH_3$ | 1.72, d (1.1) | 29.4 $CH_3$ | 1.35, s | 29.5 $CH_3$ | 1.35, s |
| 18 | 18.3 $CH_3$ | 1.55, s | 18.2 $CH_3$ | 1.72, s | 19.0 $CH_3$ | 1.60, s |
| 19 | 120.2 $CH_2$ | 5.04, s 5.10, s | 111.0 $CH_2$ | 4.65, s 4.80, s | 120.1 $CH_2$ | 5.04, s 5.10, s |
| $CH_3$ of $CH_3COO$ | 21.4 $CH_3$ | 2.06, s | 21.2 $CH_3$ | 2.07, s | 21.2 $CH_3$ | 2.04, s |
| CO of $CH_3COO$ | 170.8 qC | | 170.9 qC | | 170.4 qC | |
| $CH_3$ of $CH_3OCO$ | 51.4 $CH_3$ | 3.56, s | | | 51.2 $CH_3$ | 3.48, s |
| CO of $CH_3OCO$ | 172.7 qC | | | | 172.3 qC | |
| $CH_3O$ | | | 56.0 $CH_3$ | 3.38, s | | |
| $CH_3O$ | | | 55.0 $CH_3$ | 3.47, s | | |

Figure 5.

COMPOSITIONS AND METHODS FOR TREATING CANCER

CROSS REFERENCE TO RELATED APPLICATIONS

This application is a 35 U.S.C. §371 National Phase application of International Application Serial No. PCT/US2008/055977, filed Mar. 5, 2008, which claims priority under 35 U.S.C. §119(e) to U.S. Provisional Application Ser. No. 60/904,914, which was filed Mar. 5, 2007. The disclosures of both applications are incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of grant R37 CA53370 awarded by the National Institutes of Health.

BACKGROUND OF THE INVENTION

Soft corals belonging to the genus Xenia are a rich source of diterpenoids. Diterpenoids are secondary metabolites containing as their most characteristic and unique feature a nine-membered monocarbocyclic ring. The structures of Xenia diterpenoids have been divided into three groups: xenicins (containing a dihydropyran-cyclononane skeleton), xeniolides (possessing a δ-lactone-cyclononane skeleton), and xeniaphyllanes (with a bicyclo[7.2.0]undecane skeleton). 1,2-xenicanes combine unique structural features with interesting biological activities, specifically they are cytotoxic against several human cancer cell lines.

A major limitation in the study of natural products from marine invertebrates, especially diterpenes, has been the difficulty in obtaining these compounds in sufficient quantities. First, attempting to re-isolate reasonable amounts of the same compound from the organism is difficult given the changing natural growth environment of these organisms. Second, the framework of nine-membered rings and the particular arrangement of functional groups with multiple embedded stereocenters limit the range of chemical reactions that are applicable to their synthesis. There is little in the existing synthetic literature to define an effective strategy for the synthesis of xenicanes.

Screening of organic extracts of marine algae and cyanobacteria for mechanism-based anticancer agents has been quite productive and has led to the discovery of new chemotypes showing antiproliferative properties. Cytotoxic chemotherapeutics currently in use rely on the ability to selectively target proliferating cells, which are enriched in tumors. Unfortunately, these drugs are also cytotoxic to proliferating normal cells, accounting for the severe and potentially lethal side effects that limit dosing and effectiveness. Moreover, while sometimes effective, cytotoxic chemotherapy non-specifically damages both normal and tumor cells, with successful treatment often relying on preferential induction of cell death by apoptosis in tumor cells. Tumor cells, however, evolve apoptosis-resistance mechanisms that confound treatment necessitating the development of the therapeutic means for restoring the capacity for apoptosis in cancers. While many conventional cytotoxic chemotherapeutics trigger apoptosis indirectly by inflicting cellular damage, recent efforts have evolved to develop agents that specifically target or activate the apoptotic pathway.

SUMMARY OF THE INVENTION

The present invention is directed to diterpene compounds of formulas I-IV:

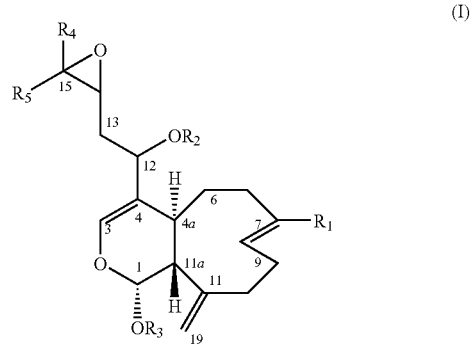

(I)

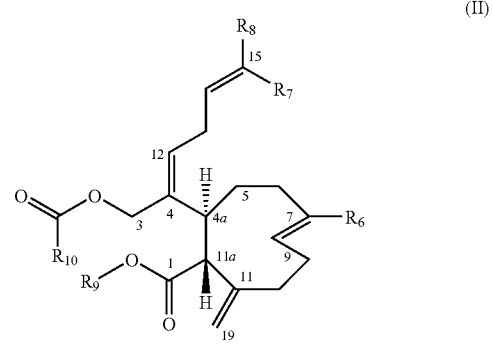

(II)

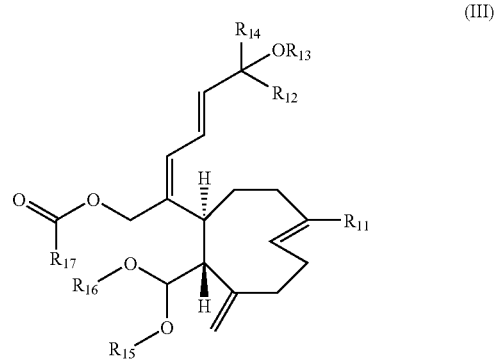

(III)

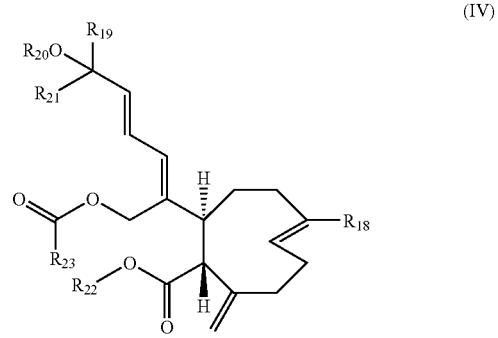

(IV)

wherein:

$R_1$ and $R_4$-$R_{23}$ are independently selected from H and 1-3 carbon lower alkyl; and $R_2$ and $R_3$ are independently selected from H, 1-3 carbon lower alkyl, and

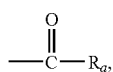

wherein $R_a$ is 1-3 carbon lower alkyl.

Also provided are pharmaceutical compositions, which include a compound of formula I-IV and a pharmaceutically acceptable carrier.

The compounds of the present invention induce tumor cell apoptosis.

Therefore, one embodiment includes methods of inducing tumor cell apoptosis by administering to a patient in need thereof an amount of a compound of formula I-IV effective to induce tumor cell apoptosis.

Also provided are methods for obtaining any of Compounds I-IV by extracting the compound from coral.

BRIEF DESCRIPTION OF THE DRAWINGS

FIG. 4 is a table listing NMR spectroscopic data for Compound I (300 MHz, CDCl$_3$); and FIG. 5 is a table listing $^1$H (300 MHz, CDCl$_3$) and $^{13}$C (75 MHz, CDCl$_3$) NMR data for Compounds II-IV.

DETAILED DESCRIPTION OF THE INVENTION

Figure 1:
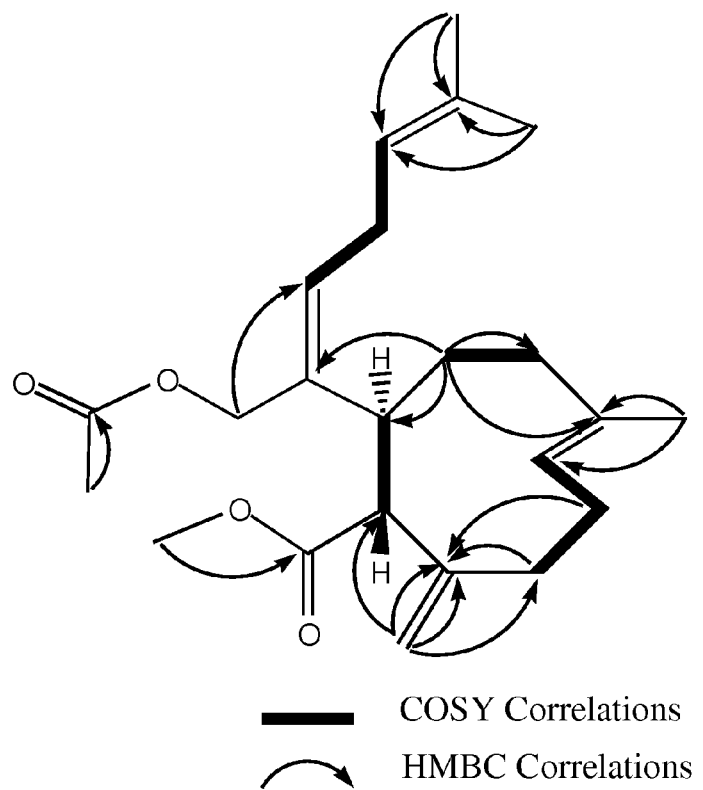
FIG. 1 depicts selected HMBC and COSY correlations for Compound II.

The present invention relates to the isolation and characterization of novel diterpenes from the soft coral Xenia elongata and the discovery of their ability to induce apoptosis in tumor cells.

With respect to Compound I, $R_1$, $R_4$, and $R_5$ are preferably methyl and $R_2$ and $R_3$ are preferably

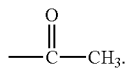

In Compound II, $R_6$-$R_{10}$ are preferably methyl. In Compound III, $R_{11}$, $R_{12}$, and $R_{14}$-$R_{17}$ are preferably methyl and $R_{13}$ is preferably hydrogen. With respect to Compound IV, $R_{18}$, $R_{19}$, and $R_{21}$-$R_{23}$ are preferably methyl and $R_{20}$ is preferably hydrogen.

Two proapoptotic Bcl-2 family member proteins, Bax and Bak, are the functionally redundant, essential downstream regulators of apoptosis in the vast majority of apoptotic signaling pathways. Bax and Bak are essential for apoptotic function required for suppressing tumor growth and for mediating chemotherapeutic response. The vast majority of human solid tumors are of epithelial origin, and defects in apoptosis, mostly upstream of Bax and Bak, play important roles in both tumor suppression and mediation of chemotherapeutic response.

The compounds of the present invention induce apoptosis upstream of Bax and Bak and can be used as anticancer agents that exploit the apoptosis pathway in tumor cells. Therefore, the present invention includes a method of inducing tumor cell apoptosis by administering to a patient in need thereof an amount of any of Compounds I-IV effective to induce tumor cell apoptosis. In one embodiment, the amount is effective to induce apoptosis upstream of Bax and Bak. Preferred tumor cells include breast tumor cells.

As used above, and throughout the description of the invention, the following terms, unless otherwise indicated, shall be understood to have the following meanings:

"Patient" means a mammal including a human.

"Effective amount" means an amount of any of Compounds I-IV effective for producing a desired therapeutic effect.

"Treat" or "treatment" or "treating" mean to lessen, eliminate, inhibit, improve, alter, or prevent a disease, condition, or disorder, for example by administration of any of Compounds I-IV.

In practice, a composition containing the any of Compounds I-IV may be administered in any variety of suitable forms, for example, orally, by inhalation, topically, parenterally, or rectally. Preferably, the composition is administered orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing any of Compounds I-IV may be presented in forms permitting administration by the most suitable route. The invention also relates to administering compositions containing any of Compounds I-IV which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions. Preferred dosage forms include tablets, capsules, oily suspensions, aqueous suspensions, lozenges, troches, powders, granules, emulsions, syrups, and elixirs.

The choice of vehicle is generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, any of Compounds I-IV may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of any of Compounds I-IV as a free base or pharmacologically acceptable salt can be prepared in water suitably mixed with a surfactant such as hydroxypropyl-cellulose. Dispersions can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating any of Compounds I-IV in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing any of Compounds I-IV may be used. Any of Compounds I-IV may be also incorporated in a gel or matrix base for application in a patch, which would allow a controlled release of compound through transdermal barrier.

For administration by inhalation, any of Compounds I-IV may be dissolved or suspended in a suitable carrier for use in a nebulizer or a suspension or solution aerosol, or may be absorbed or adsorbed onto a suitable solid carrier for use in a dry powder inhaler.

The percentage of Compounds I-IV in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

Compounds I-IV used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, any of Compounds I-IV may be administered 1 to 4 times per day. Of course, for other patients, it will be necessary to prescribe not more than one or two doses per day.

The following non-limiting examples set forth herein below illustrate certain aspects of the invention.

EXAMPLES

Instrumentation and Solvents

Optical rotations were measured on a JASCO P 1010 polarimeter. UV and FT-IR spectra were obtained employing Hewlett Packard 8452A and Nicolet 510 instruments, respectively. All NMR spectra were recorded on a Bruker Avance DRX300 and DPX400 spectrometers. Spectra were referenced to residual solvent signal with resonances at $\delta H/C$ 7.26/77.1 ($CDCl_3$). ESI MS data were acquired on a Waters Micromass LCT Classic mass spectrometer and Varian 500-MS LC Ion Trap. HPLC separations were performed using Waters 510 HPLC pumps, a water 717 plus autosampler, and Waters 996 photodiode array detector. All solvents were purchased as HPLC grade.

Example 1

Extraction and Isolation of Compounds I-IV

Live colonies of Xenia elongata were kept in optimal growing conditions (Salinity 34 g/L, Temperature 25° C., Light [min. 250 $\mu Em^{-2}s^{-1}$ and max. 500 $\mu Em^{-2}s^{-1}$], pH 8.2-8.4) in the coral laboratory at the Marine Biotechnology Center, Institute of Marine and Coastal Sciences, Rutgers University. A voucher specimen is available as collection number SC/XE/Apr-04 System 1A. The soft coral was stored at −80° C. after addition of liquid nitrogen before workup.

The material (80 g) was extracted three times, first with $CH_2Cl_2$ and then with MeOH, to give non polar crude organic extract (259.2 mg) and polar crude organic extract (537.9 mg). A portion of these two extracts (30 mg each) was tested for apoptosis induction. The polar crude organic extract was found active and subjected to fractionation by solid phase extraction cartridge (Reverse-phase C18) to give three fractions using a stepwise gradient of water-MeOH as solvent system. The fraction eluting with 15% water and 85% MeOH had apoptosis induction activity. This fraction was further chromatographed on analytical reverse-phase HPLC (Phenomenex luna C8, 250×4.60 mm) using gradient elution system (starting with 80% water and 20% acetonitrile, flow rate 1 mL/mn) to yield successively 2.1 mg of Compound III ($t_R$=26 min), 4.3 mg of Compound I ($t_R$=29 min), 3 mg of Compound IV ($t_R$=31 min), and 3 mg of Compound II ($t_R$=35 min).

Extraction of Xenia elongata with non-alcoholic solvent was performed with $CH_2Cl_2$. The material (40 g) was extracted four times with $CH_2Cl_2$ to give crude organic extract (200 mg). This extract was fractionated by solid phase extraction cartridge (Normal-phase) to give three fractions using a stepwise gradient of n-hexane-EtOAc as the solvent system. The fraction eluting with 50% n-hexane and 50% EtOAc was further chromatographed on analytical reverse-phase HPLC (Phenomenex luna C8, 250×4.60 mm) using a gradient elution (starting with 80% $H_2O$ and 20% acetonitrile, flow rate 1 mL/mn) to yield successively 1 mg of Compound III ($t_R$=26 min), 1.3 mg of Compound IV ($t_R$=31 min), and 1.5 mg of Compound II ($t_R$=35 min).

The molecular formula of Compound I was established as $C_{24}H_{34}O_6$ on the basis of high resolution electron spray ionization mass spectrometry (HRESIMS) [m/z 441.2250 $(M+Na)^+$ (calculated for $C_{24}H_{34}O_6Na$, 441.2253)]. This indicated a difference of an acetate group by comparison to the known compound xeniculin isolated from Xenia macrospiculata. The $^1H$ NMR of Compound I indicated the existence of the following functional groups: an 1-acetoxydihydropyran moiety [δ5.87 (d, J=1.8 Hz), H-1 and 6.55 (s, H-3], a terminal methylene [≠74.78 (s) and 4.87 (s), H-19, H-19']two methyls a to oxygen [δ1.29 (s), H-16,H-17], an epoxy signal at [δ2.73 (t, J=5.9 Hz), H-14], and vinyl methyl [1.66 (s), H-18]. The NMR spectra of Compound I and xeniculin were compared in $CDCl_3$ and were found to be similar, with the exception of the presence of a methylene group at C-9 [δ25.1] instead of oxygen bearing carbon in xeniculin [δ70.6], suggesting that 1 is 9-deacetoxyxeniculin. This suggests that Compound I is 9-deacetoxyxeniculin.

The relative stereochemistry of Compound I was established on the basis of ROESY data, coupling constant analyses, and chemical shift comparison to xeninculin, tsitsixenicin A, and related compounds. The coupling constant (J=12 Hz) between H-4a and H-11a suggests a trans ring junction. The small coupling constant (J=1.3 Hz) between H-1 and H-11a would favor the a-position for H-1 if the six-member ring was in a quasi-boat conformation. A closer look of the crystal structure of xenicin and essentially the six-member ring (1-acetoxydihydropyran moiety), which is also present in Compound I, suggests that H-1, if it is in the α-position, should display a ROESY cross peak correlation to H-4a. In order to verify this suggestion, a high scan ROESY experiment was performed. Analysis of the ROESY data, particularly in the cross peak region of H-1 and H-4a, revealed unambiguously that these two protons display a ROESY correlation. Based on this result, it appears that the configurations at C-1, C-4a, and C-11a in Compound I are essentially the same as those in xeninculin, in which the protons H-1 and H-4a are on the a face of the ring and the proton H-11a is oriented on the β-side. Previous attempts to establish the stereochemistry of an acetate group at C-12 in xenicane diterpenes by chemical transformations and spectroscopy have failed, and therefore the stereochemistry at C-12 remains unassigned. From the above results, the structure of Compound I was formulated.

A molecular formula of $C_{23}H_{34}O_4$ for Compound II was determined from HRESIMS data. $^1H$, $^{13}C$ NMR, DEPT, and multiplicity-edited HSQC of Compound II indicated the presence of three olefinic methyl groups [δ18, 18.3, 25.5, C-16, C-18, C-17], five methylene groups [δ28, 28.9, 32.5, 32.6, 39.9, C-13, C-9, C-5, C-10, C-6], two methine groups [δ39.9, 61.7, C-4a, C-11a], one oxygen bearing methylene group [δ66.5, C-3], one exocyclic methylene group [δ120.2, 144.2, C-19, C-11], three trisubstituted olefins [(δ121.0, 133.5, C-14,C-15), (δ139.5, 130, C-4,C-12), (δ124.6,136, C-7,C-8)], two carbonyls [δ172.7, 170.8, C-1,C-3], one methyl belonging to the acetate group [δ21.4] and one methyl ester [δ51.4]. Based on the COSY and HMBC correlations (FIG. 1), Compound II was considered to be a nine-membered monocarbocyclic ring belonging to the xenicane-type diterpenoid. Furthermore, the NMR spectra of Compound II were similar to those of umbellacin F, except that the diol at C-14 and C-15 was missing in Compound II and replaced by a double bond between C-14 and C-15, this suggests that umbellacin F is the corresponding diol of Compound II.

The relative stereostructure of Compound II was investigated with the aid of a ROESY spectrum. The E-configuration was assigned to $\Delta^{4(12)}$ double bond based on the observed ROESY cross peak between H-13b [δ2.85] and H-4a [δ3.30]. The E-configuration of the $\Delta^{7(8)}$ double bond was suggested by the observed ROESY cross peak between H-18 [δ1.55] and H-9a [δ2.10]. The configuration of the two chiral centers at C-4a and C-11a was deduced by ROESY data and comparison with those of umbellacin F. The large coupling constant (J=11 Hz) between H-4a [δ3.30] and H-11a [δ3.12] suggests that they have a configuration opposite each other. The observed ROESY cross peak between H-3 [δ4.53] and H-11a [δ3.12] suggests that they have the same configuration as that of umbellacin F. Therefore, the structure of Compound II was established.

The IR spectrum of Compound III exhibited absorptions due to hydroxyl (3460 $cm^{-1}$) and carbonyl (1736 $cm^{-1}$) groups. HRESIMS and NMR data of Compound III suggests a molecular formula of $C_{24}H_{38}O_5$. The NMR features of Compound III closely resemble those of xenibecin with the exception that an acetate group appears in Compound III and one oxygen bearing methylene [δ65.3, C-3] is also noticed in Compound III. The strong HMBC correlations between the two methyl groups at δ3.38 and δ3.47 to the carbon at δ105.0, C-1 suggest that these two methoxy groups are attached to the same carbon C-1 in contrast to that found in xenibecin in which one methoxy group was attached to carbon C-1 and the other methoxy group was attached to carbon C-3. The $^1H$ and COSY NMR spectra of Compound III displayed an E-diene system at δ6.00 (d, J=11, H-12), δ6.43 (dd, J=11, 15, H-13) and δ5.93 (d, J=15, H-14). The olefinic methyl [δ1.72 (s), H-18] and the exocyclic methylene [δ4.65 (s), 4.80(s), H-19, H-19'] were also present in Compound III as well as in xenibecin. One oxygen bearing carbon [δ70.8, C-15] was also noticed in Compound III at the same position as that in xenibecin. These above results indicate that the structure of Compound III is like xenibecin except that Compound III is a nine-membered monocarbocyclic ring whereas xenibecin is a trans-fused bicyclic ring.

The relative configuration of the two chiral centers at C-4a and C-11a was established using a ROESY experiment, coupling constant analyses, and chemical shift comparison to umbellacin G, xenibecin, and xenitacin. The large coupling constant J=11.5 Hz between H-4a and H-11a combined with the observed ROESY cross peak between H-11a [δ3.45] and H-3 [δ4.53] indicated that the relative configuration of C-4a and C-11a are similar to that of xenibecin. From these results the structure of Compound III was formulated as shown.

The HRESIMS of Compound IV revealed that the molecular formula was $C_{23}H_{34}O_5$. The NMR data of Compound IV is similar to Compound III with the exception that only one methoxy group [δ3.48] was present in $^1H$ NMR of Compound IV. The $^{13}C$ and HMBC data indicated two carbonyl signals: one belongs to the acetate group [δ170.3] attached to C-3 and the other one is the carbonyl [δ172.30, C-1] of the methyl ester moiety. The NMR data of Compound IV was also compared to that of xenibecin, florlide F, and 9-deoxy-isoxeniolide-A which led to the conclusion that the structure of Compound IV is analogous to florlide F with the only difference in the ring system that resembles to xenibecin and in 9-deoxy-isoxeniolide-A.

Figure 2:
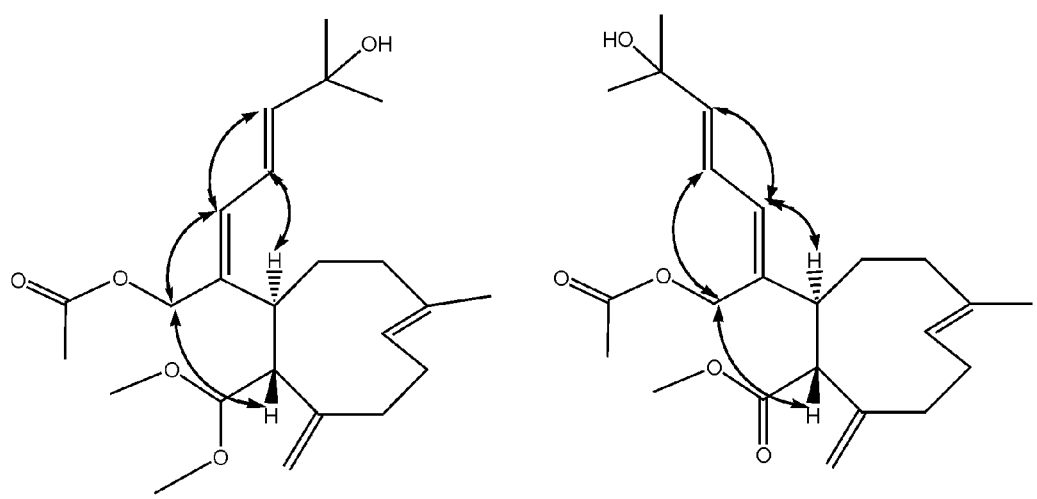
FIG. 2 depicts selected ROESY cross peaks for Compounds III and IV.

The relative configuration at C-4a and C-11a was deduced by ROESY data. The observed ROESY cross peak between H-3, δ4.53 and H-11a, δ3.13 combined with the large coupling constant (J=12 Hz) between H-4a and H-11a suggested that they have trans configuration and are comparable to H-4a (α-oriented) and H-11a (β-oriented), found in Compound III as well as in xenibecin. The E-diene system was confirmed by the observed ROESY cross peak between H-12, H-14 and H-13, H-3 (FIG. 2). Therefore the structure of Compound IV was established.

The use of methanol in the isolation procedure raises the question whether the methyl esters at C-1 in Compounds II and IV and the two methyl ethers in Compound III are "true" natural products, or if they are adduct "artifacts" produced during the isolation process. To address this issue the soft coral Xenia elongata was extracted with $CH_2Cl_2$. After fractionation by solid phase extraction, followed by HPLC isolation, the chromatogram was compared to that of the fraction originally extracted by methanol. The comparison revealed that the three Compounds (II-IV) were also present in the chromatogram from the fraction originally extracted by $CH_2Cl_2$. These three compounds were collected and analyzed by mass spectrometry and proton NMR. The results confirmed that Compounds II-IV are, indeed, natural products. Thus, the four diterpenoid compounds possess similar structures, which parallel their ability to induce apoptosis.

Example 2

Evaluation of Apoptosis Induction

Apoptosis induction of W2 (apoptosis competent) cells and growth of D3 (apoptosis defective) cells in the presence of Compounds I-IV was examined. Pro-apoptotic Bax and Bak are the essential and redundant regulators of apoptosis required for suppressing tumor growth and chemotherapeutic response. Because D3 cells are genetically deleted for Bax and Bak, there is no means to restore apoptosis in these cells, yet all apoptosis regulatory mechanisms upstream (Bcl-2, Bcl-xL, Bim, Nbk/Bik, Puma, Noxa, caspase-3, caspase-7) remain intact. Because the vast majority of human cancers have disabled apoptosis upstream of Bax and Bak, this screen should identify compounds that have the capacity to activate apoptosis upstream of, and those that require, Bax and Bak. This feature permits the use of W2 and D3 cell lines in biological screening for compounds that promote apoptosis by the criteria of killing W2 and not D3 cells. Compounds that indiscriminately kill both apoptosis-competent W2 and apoptosis-defective D3 cells are eliminated as non-specifically toxic.

W2 and D3 cells were plated in 96 and 24-well plates and incubated for 24 hours after which they were evenly spread at about 50% confluency. At this time, compounds dissolved in DMSO and diluted in growth medium (DMEM) were added to the cells at various concentrations. DMSO concentration was kept at 0.5% in all wells. Plates were incubated for 24, 48, and 72 hours. Cell viability was determined using a modification of the MTT assay, where the reduction of yellow tertazolium salt (MTT-3-(4,5-Dimethylthiazol-2-yl)-2,5) to purple formazan indicates mitochondrial activity, and thus cell viability. Cells were incubated with 0.5 mg/ml MTT for 3 hours. Supernatant was aspirated, and DMSO was added to dissolve the formazan crystals. After 30 minutes incubation at 37° C., with shaking, absorbance was read at 570 nm on a Spectra MAX 250 (Molecular Devices) plate reader. Differential growth from time 0 to 48 hours was calculated. Staurosporine, an apoptosis inducer, and DMSO were used as positive and negative controls, respectively. Cells incubated with compounds in 24 well plates were visualized microscopically and digital images were captured. Apoptosis induction was calculated as the difference in viability between time 0 (addition of compound) and 48 hours, and is defined as at least 20% death of W2 cells, and a 10% or higher growth of D3 cells.

Figure 3:
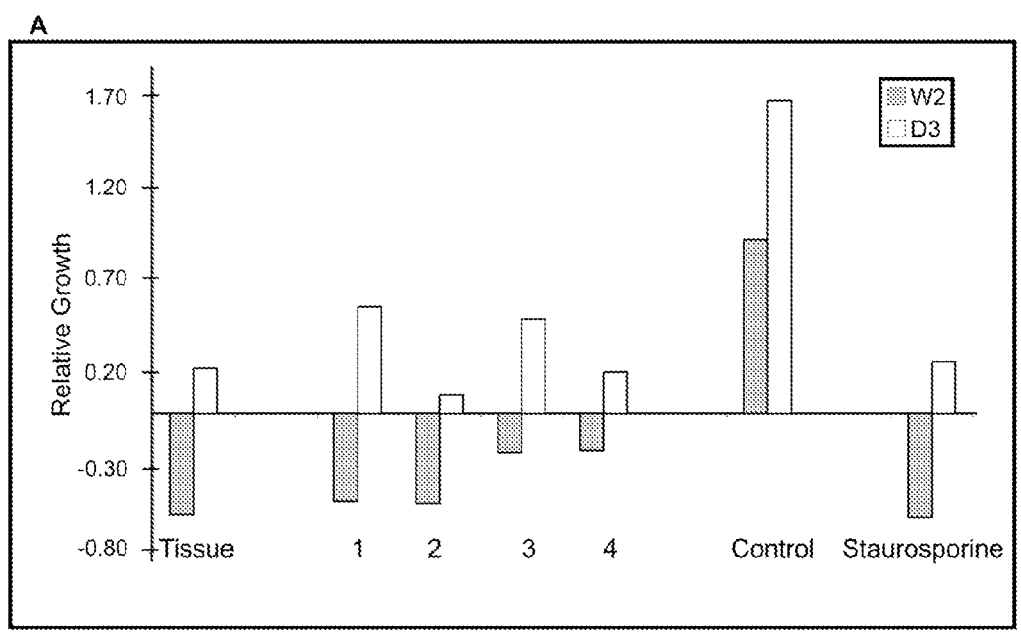
FIG. 3a is a plot of the change in relative W2 and D3 cell viability by MTT assay 48 hours after addition of whole tissue extract and Compounds I-IV (1-4). (1-12 µM, 2-29 µM, 3-12 µM, 4-11 µM). Values for the compounds are an average of five wells, with a standard deviation of less than 15% of the mean.
FIG. 3b is a series of time-lapse microscopy images of the apoptosis competent W2 cells and the apoptosis resistant D3 cells that were cultured in the presence or absence of Compound I (12 µM) under normal physiological conditions (DMEM with 10% FBS, 5% CO2 at 37° C.)
Figure 3:
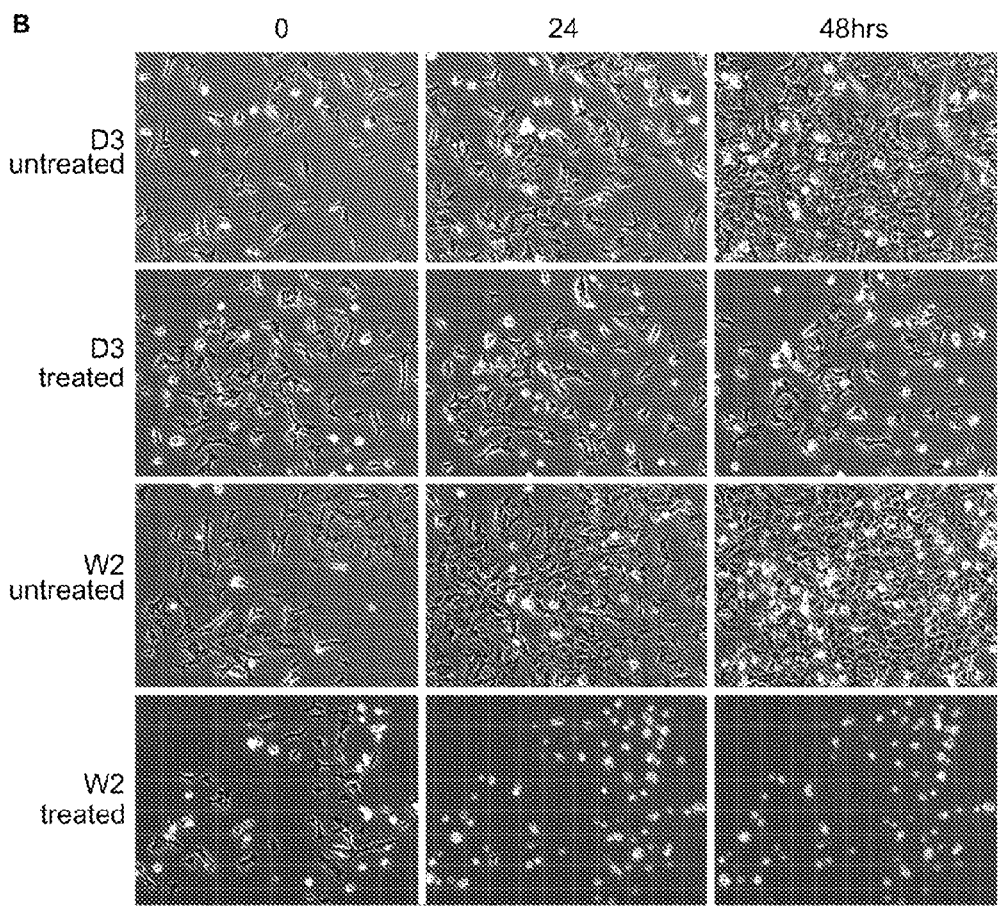

The results (FIG. 3a) reveal a significant induction of apoptosis by the whole tissue extract and by individual compounds, with the most remarkable induction shown by Compound I (61% growth of D3 and 50% death of W2). Treatment of W2 and D3 cells with 0.1 μM staurosporine, a protein kinase inhibitor and potent inducer of apoptosis, was included as a positive control for apoptosis induction for comparison, which induced apoptosis at comparable levels to Compound I (FIG. 3a). Thus, the diterpenes of the present invention effectively and specifically activate apoptosis in immortalized mammalian epithelial cells.

In order to determine the differential impact of apoptosis induction on cell growth and viability of W2 and D3 cells, cell division and viability was monitored via time-lapse microscopy. Cells were cultured in a time-lapse chamber equipped with controlled environmental conditions. The time-lapse microscopy system consisted of an Olympus IX71 inverted microscope fitted with temperature, humidity and $CO_2$ controlled environmental chamber (Solent Scientific, UK) and a Coolsnap ES cooled CCD camera. Image capturing and analysis were performed using Image-Pro Plus software (Media Cybernetics, USA). Phase contrast images (100×) at multiple fields were obtained for the indicated time period. Time-lapse images were converted to movies using Image-Pro Plus software with custom modifications and a graphic data processing workstation (Dell Precision 670).

W2 and D3 cells were incubated for 48 hours in the presence of Compound I (12 mM) (FIG. 3b). Both W2 and D3 cell lines showed comparable cell viability in the absence of the drug (FIG. 3b). D3 cells retained their viability in presence of Compound I even at 48 hours, and this viability persisted following 72 hours of treatment. There was, however, clear indication of growth arrest in the treated D3 cells. In contrast, W2 cells were highly sensitive to apoptosis induced by Compound I. The apoptosis-competent W2 cells became rounded and detached from the surface between 18-24 hours of treatment, displaying classic apoptotic morphology by time-lapse microscopy. Survival of the D3 cells for at least 72 hours in contrast to the induction of cell death of W2 cells within 18-24 hours of treatment with Compound I suggest that Compound I induced Bax- and Bak-mediated apoptosis. Taken together, these observations suggest that Compound I induces apoptosis when the apoptosis pathway is intact, and mediates cell growth arrest in the absence of a functional apoptosis pathway.

Example 3

Connectivity Analysis for MCF-7 Breast Cancer Cells Treated with a Diterpene Compound 1.6 mg of a diterpene compound of the present invention was used to prepare a 0.12 M stock solution in DMSO. Proliferating MCF-7 breast cancer cells were treated in triplicate with either a 120 μM final concentration of diterpene compound (final DMSO concentration 0.1%), or were left untreated for 8 hours. Cells were harvested and RNA extracted using TRIzol Reagent, (Invitrogen, Carlsbad, Calif., USA) and RNeasy kit (Qiagen Sciences, Md., USA).

RNA was purified, reverse transcribed, and hybridized to an Affymetrix U133 2.0 array by the CINJ Transcriptional Profiling Core.

Two methods were used to identify the most differentially expressed genes in the treated versus control groups. The first method (significance analysis of arrays) was set at a false discovery rate of 3.58%, and yielded 215 genes. A subset of these 215 genes, including 145 with at least a 3-fold difference in expression (58 upregulated by treatment, 87 down-regulated), was defined as the diterpene signature, and was used for the Connectivity analysis. The diterpene signature was compared to 453 gene expression profiles present in the Connectivity Map (http://www.broad.mit.edu/cmap/). For each of the 453 profiles, a connectivity score was calculated (based on the Kolmogorov-Smirnov statistic), which represents the relative similarity of the profile to the diterpene signature.

Common drug targets among the mostly highly connected instances include the proteasome, calmodulin, and histone deacetylases (HDACs). The presence of structurally distinct compounds that yield high connectivity scores suggests that the diterpene compound of the present invention acts as a proteasome and calmodulin inhibitor. Conversely, instances associated with the most highly ranked negative scores (corresponding to a gene expression profile similar to a reversal of the diterpene signature) include compounds that target the PI3 kinase/mTOR pathway. Additional inferences can be made from "permuted results" provided by the Connectivity analysis (Table 1). In particular, analysis of permuted results supports the idea that the diterpene compound is affecting cells in a manner similar to that of HSP90 and HDAC inhibitors and in a manner opposite to that of PI3 kinase/mTOR inhibitors. Note that the proteasome inhibitors are not included in the permuted results because they are represented by single instances.

TABLE 1

Permutted Results.

| Rank | CMAP name | Score | N | Enrichment | P value | Target |
|---|---|---|---|---|---|---|
| 1 | sirolimus | −0.254 | 10 | −0.770 | 0.0000 | mTOR |
| 2 | 17-allylamino-geldanamycin | 0.496 | 18 | 0.611 | 0.0000 | HSP90 |
| 3 | trichostatin A | 0.565 | 12 | 0.714 | 0.0000 | HDACs |
| 4 | LY-294002 | −0.038 | 17 | −0.506 | 0.0001 | PI3 kinase |
| 5 | geldanamycin | 0.544 | 6 | 0.759 | 0.0004 | HSP90 |
| 6 | 5253409 | 0.748 | 2 | 0.971 | 0.0009 | ? |
| 7 | 5224221 | 0.758 | 2 | 0.967 | 0.0015 | ? |
| 8 | vorinostat | 0.684 | 2 | 0.956 | 0.0032 | HDAC |
| 9 | tetraethylenepentamine | −0.084 | 6 | −0.662 | 0.0055 | proteases |
| 10 | wortmannin | −0.248 | 8 | −0.565 | 0.0071 | PI3 kinase |

Each row in the table summarizes the performance of all instances produced with the same perturbagen. The table displays the cmap name for those perturbagens, the arithmetic mean of the connectivity scores for each of those instances (labeled "score"), the number of those instances (labeled "n"), a measure of the enrichment of those instances in the list of all instances ordered by descending order of connectivity score and up score (labeled "enrichment"), and a permutation p-value for that enrichment score (labeled "p"). Enrichment scores and p-values are not provided for perturbagens represented by only one instance or where the mean of the connectivity scores for their instances is zero.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. An isolated compound selected from the group consisting of formulas I, II, III, and IV:

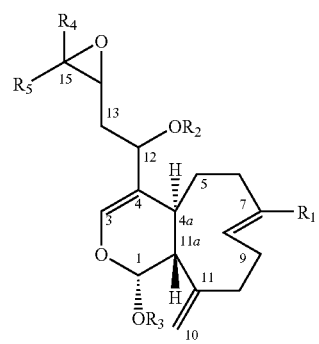

(I)

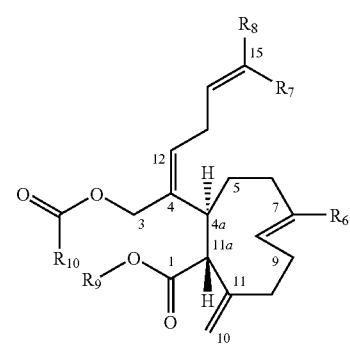

(II)

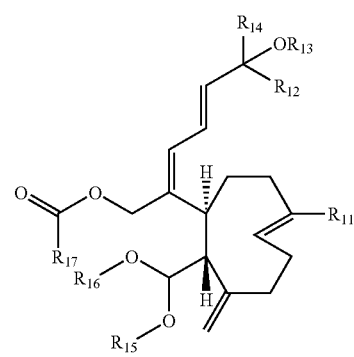

(III)

-continued (IV)

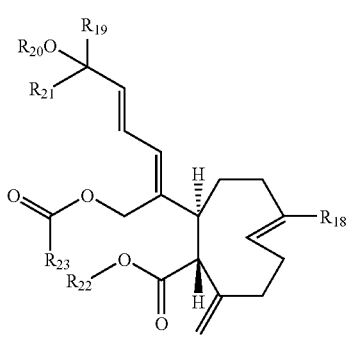

wherein:
R₁ and R₄-R₂₃ are independently selected from the group consisting of H and 1-3 carbon lower alkyl; and
R₂ and R₃ are independently selected from the group consisting of H, 1-3 carbon lower alkyl, and

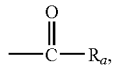

wherein $R_a$ is 1-3 carbon lower alkyl.

2. The compound of claim 1 comprising formula (I), wherein $R_1$, $R_4$, and $R_5$ are methyl and $R_2$ and $R_3$ are

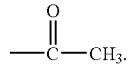

3. The compound of claim 1 comprising formula (II), wherein $R_6$-$R_{10}$ are methyl.

4. The compound of claim 1 comprising formula (III), wherein $R_{11}$, $R_{12}$, and $R_{14}$-$R_{17}$ are methyl and $R_{13}$ is hydrogen.

5. The compound of claim 1 comprising formula (IV), wherein $R_{18}$, $R_{19}$, and $R_{21}$-$R_{23}$ are methyl and $R_{20}$ is hydrogen.

6. A pharmaceutical composition comprising a compound of claim 1 and a pharmaceutically acceptable carrier.

7. A method of inducing tumor cell apoptosis comprising administering to a patient in need thereof an amount of a compound of claim 1 effective to induce tumor cell apoptosis.

8. The method of claim 7, wherein said amount is effective to induce apoptosis upstream of Bax and Bak.

9. The method of claim 8, wherein said tumor cell is a breast tumor cell.

10. A method of obtaining a compound of claim 1 comprising extracting the compound from coral.

11. The method of claim 10, wherein said coral is soft coral.

12. The method of claim 11, wherein said soft coral is Xenia elongata.

* * * * *